United States Patent [19]

Kim et al.

[11] 4,198,352

[45] Apr. 15, 1980

[54] INTERNAL OLEFIN HYDROFORMYLATION PROCESS

[75] Inventors: Leo Kim, Sittingbourne, England; Sunny C. Tang, Houston, Tex.

[73] Assignee: Shell Oil Company, Houston, Tex.

[21] Appl. No.: 964,319

[22] Filed: Nov. 29, 1978

[51] Int. Cl.$^2$ ............................................. C07C 45/10
[52] U.S. Cl. ............................................. 260/604 HF
[58] Field of Search ................. 260/604 HF, 632 HF; 568/909

[56] References Cited

U.S. PATENT DOCUMENTS

| | | | |
|---|---|---|---|
| 3,527,809 | 9/1970 | Pruett | 260/604 HF |
| 3,981,925 | 9/1976 | Schwager et al. | 260/604 HF |
| 3,996,293 | 12/1976 | Knifton et al. | 260/604 HF |

OTHER PUBLICATIONS

J. Am. Chem. Soc. vol. 99, p. 1986 (1977).

*Primary Examiner*—Werren B. Lone
*Attorney, Agent, or Firm*—Howard W. Haworth

[57] ABSTRACT

Internal olefins are hydroformylated to linear aldehydes in substantial amounts by contacting the internal olefins with hydrogen, carbon monoxide and a catalyst comprising a ligand stabilized ionic platinum compound of the general formula $PtCl(CO)(Ligand)_2{}^+An^-$ complexed with a modifying metal halide selected from tin, zinc, or germanium halides.

4 Claims, No Drawings

INTERNAL OLEFIN HYDROFORMYLATION PROCESS

BACKGROUND OF THE INVENTION

1. Field of the Invention

This invention relates to the addition of hydrogen and carbon monoxide to internal olefins to obtain substantial amounts of linear aldehydes.

2. Description of the Prior Art

Aldehydes, particularly linear aldehydes, are extremely useful as intermediates in organic synthesis because of their terminal carbonyl group which is among the most active groupings in organic compounds. For instance, they are easily reduced and oxidized and take part in a number of addition reactions. More specifically, aldehydes are readily catalytically reduced to the primary alcohols, and oxidized to the corresponding carboxylic acids. They also undergo addition and/or condensation reactions with hydrogen cyanide, alcohols, nitroparaffins as well as condensations with themselves and other carbonyl-containing compounds. Further, these aldehydes condense with ammonia and its derivatives including primary amines. The latter condensation products (which are commonly known as Schiff's bases) lend themselves to applications as surfactants or detergents when solubilized by processes such as sulfation or oxyalkylation.

Generally, aldehydes as a class are produced commercially by the catalytic addition of carbon monoxide and hydrogen to olefins in a process known as hydroformylation. In contrast to the abundance of information in the literature on the hydroformylation of alpha-olefins, there is a dearth of published information on the hydroformylation of internal olefins. This is undoubtedly attributable to the differences in reactivity between the various isomeric olefins. Generally, the nearer the double bond is to the terminal position, the higher is the reactivity. Whereas it is relatively easy to achieve high aldehyde linearity (>90%) in the hydroformylation of alpha-olefin, using for examples $Rh/P(OPhCl)_3$ (Pruett and Smith, U.S. Pat. No. 3,527,809 issued Sept. 8, 1970) or $PtCl_2(PPh_3)_2/SnCl_2$ (Schwager and Knifton, U.S. Pat. No. 3,981,925 issued Sept. 21, 1976), the catalytic hydroformylation of internal olefins to yield exclusively or predominantly terminal aldehydes is unknown. Catalysts to convert internal olefins to linear aldehydes must perform a dual function; isomerization and then hydroformylation. Recently, Pittman and coworkers (J. Am. Chem. Soc., 99, 1986(1977) has reported the use of cobalt cluster catalysts to hydroformylate 2-pentene to give moderate aldehyde linearity. Schwager and Knifton (U.S. Pat. No. 3,981,925 issued Sept. 21, 1976 and U.S. Pat. No. 3,996,293 issued Dec. 7, 1976) report the conversion of 2-heptane to aldehydes in low yield and low linearity using as a catalyst a ligand stabilized platinum (II) dehalide complexed with Group IVA metal halides.

SUMMARY OF THE INVENTION

This invention relates to a process for converting internal olefins to linear aldehydes in substantial amounts by means of a hydroformylation reaction and a catalyst comprising a ligand stabilized ionic platinum compound complexed with a Group IVA metal halide. Other catalysts such as the platinum (II) dihalides provide insignificant yields of linear aldehydes. The catalyst of the present invention provides isomerization activity in addition to hydroformylation activity which allows the production of significant quantities of linear aldehydes from internal olefins.

DESCRIPTION OF THE PREFERRED EMBODIMENTS

In the broadest contemplated practice of the invention, substantial quantities of linear aldehydes are produced from internal olefins by a catalytically directed addition of hydrogen and carbon monoxide to said olefins by contacting at least a catalytic quantity of catalyst comprising a ligand stabilized cationic platinum carbonyl halide moiety, a non-coordinating anionic moiety and a Group IVA metal halide.

In a preferred specific embodiment of the above described process, internal olefins having carbon numbers from 4 to about 30 are hydroformylated by the catalytic addition of hydrogen and carbon monoxide to produce substantial amounts of linear aldehydes by contacting the olefins with hydrogen and carbon monoxide in the presence of a catalyst comprising:

(a) a platinum complex having the following formula:

whereas $An^-$ is selected from the group consisting of $BPh_4^-$, $BF_4^-$, $ClO_4^-$, $PF_6^-$, $NO_3^-$ and $SiF_6^{--}$ and L is a stabilizing ligand having the formula:

wherein B is selected from the group consisting of phosphorus, arsenic, antimony and bismuth, R is selected from the group consisting of aryl, alkyl, aralkyl and alkaryl with less than 20 carbon atoms, a is an integer from 0 to 3, b has a value of 3-a; and (b) a modifying metal halide selected from the group consisting of $SnCl_2$, $ZnCl_2$ and $GeCl_2$ wherein the mole ratio of said metal halide to said platinum complex ranges from about 1 to about 100.

The platinum complexes of the present invention are ionic compounds having a non-complexing anionic moiety. These have the general formula:

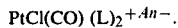

In this formula the cationic platinum moiety is $PtCl(CO)(L_2)^+$ and the non-coordinating anionic moiety $An^-$ is exemplified by $BPh_4^-$, $BF_4^-$, $ClO_4^-$, $PF_6^-$, $NO_3^-$ and $SiF_6^{--}$. In the above formula L is a stabilizing ligand and has the general formula:

wherein B represents the element from Group VA, preferably is phosphorous, arsenic, antimony or bismuth, most preferably phosphorus, R is aryl, alkyl, aralkyl or alkaryl groups which contain less than 20 carbon atoms, preferably less than 12 carbon atoms and need not be the same, O is oxygen, a has a value of 0 to 3, and b has a value 3-a. It is also suitable for the organic radical R to contain functional groups, or to satisfy more than one of the valences of the Group VA atom, thereby forming a heterocyclic compound with the group VA atoms. Alternatively the formula for the ligand can be expressed as $R_c^1 R_d^2 R_e^3 P(OR^4)_f (OR^5)_g (OR^6)_h$ where c, d, e, f, g and h individually equals 0 or 1, c+d+e+f+g+h equals 3 and R is as defined above.

The stabilizing ligand may be present in stoichiometric proportions as required by the platinum compound, i.e. two moles of ligand per mole of platinum, or may preferably be in excess, e.g. a molar excess of about 0.001 to about 10 molar excess preferably from about 0.001 to about 5 molar excess.

In accordance with the present invention, internal olefins are converted selectively to linear aldehydes having one more carbon atom than the olefinic compounds by reacting the olefinic compounds with carbon monoxide and hydrogen at temperatures from about 25° C. to about 180° C. or preferably about 50° C. to about 140° C. and at a total pressure of from about 5 kg/cm² to about 200 kg/cm² preferably from about 5 to 140 kg/cm₂, although higher pressures may be employed in the presence of the platinum catalyst described herein. In carrying out the typical hydroformylation reaction selectively to produce aldehydes it is necessary to supply one mole of carbon monoxide and one mole of hydrogen for each mole of olefin reacted. Excess carbon monoxide or hydrogen over the aforesaid stoichiometric amounts, however, may be present. Any ratio of $H_2$ to CO from 10:1 to 1:10 may be chosen.

The term stabilizing ligand used throughout this specification means a tertiary organo phosphorus compound, or a tertiary organo arsenic compound, or a tertiary organo antimony compound or a tertiary organo bismuth compound.

Suitable organo phosphorus, organo arsenic, organo antimony and organo bismuth stabilizing ligands which may comprise part of the ionic platinum coordination compound are those containing trivalent phosphorus, arsenic, antimony or bismuth atoms and are referred to as phosphines, phosphites, phosphinites and phosphonites, arsines, arsites, arsinites and arsonites, stibines, stibites, stibinites and stibonites, bismuthines, bismuthites, bismuthinites and bismuthonites.

In this group of suitable stabilizing ligands, the individual phosphorus, arsenic, antimony and bismuth atoms have one available or unshared pair of electrons. An organic derivative of the phosphorus, arsenic, antimony or bismuth with the foregoing electronic configuration is, therefore, a suitable ligand for the platinum containing catalyst of this invention. Organic radicals of any size and composition may be bonded to the phosphorus, arsenic, antimony or bismuth atoms, and the radicals are preferably selected from the group consisting of aryl, aryloxy, alkyl, and alkoxy groups. The more preferred ligands are those consisting of at least one but preferably two or three aryl-and/or aryloxy groups as the organic moieties. For example, preferred modifying ligands are illustrated by the following structural formulae, $MR_3$ where M is P, As Sb or Bi and R is i.e. phenyl ($C_6H_5$—), phenoxy ($C_6H_5O$—), or tolyl ($CH_3(C_6H_4)$—), xylyl ($CH_3C_6H_3CH_3$—), e.g. $P(C_6H_5)_3$, $P(C_6H_5O)_3$, $As(C_6H_5)_3$, $Sb(C_6H_5)_3$, $P[CH_3(C_6H_4)]_3$.

The more preferred group of stabilizing ligands includes the triphenylphosphines, triphenylphosphites, triphenylarsines, and triphenylarsites. The preferred component is the aryl or aryloxy group, e.g., the phenyl or phenoxy radical. However, the molecule may also contain some aryl groups in addition to the aryloxy radical.

The stabilizing ligands, and, if desired, other ligands, satisfy the coordination number of the central platinum atom, and thus form a platinum-containing cationic complex. The term coordination compound or coordination complex means a compound or complex formed by combination of one or more electronically rich molecules or atoms, e.g., triphenylphosphines, carbon monoxide, 1,5-cyclooctadiene, with one or more electronically poor molecules or atoms, e.g., platinum.

The metals forming the modifying metal halides are selected from the group consisting of tin, zinc and germanium. The halides comprise fluoride, chloride, bromide, iodide and the pseudohalides, such as for example borontetrafluoride, cyanide, cyanate and thiocyanate. These suitable examples of the modifying metal halides are $SnF_2$, $SnCl_2$, $SnBr_2$, $SnI_2$, $Sn(BF_4)_2$, $SnCl_4$, $Zn(CN)_2$, $Zn(SCN)_2$, $GeI_2$, $GeCl_4$, $ZnCl_2$, $ZnBr_2$, and $ZnI_2$.

The proportions of the platinum catalyst in the reaction zone, e.g. in the liquid phase relative to the olefin feed are not particularly critical but are chosen so as to maintain a homogeneous liquid medium. In general, higher concentrations of catalysts produce a faster reaction rate. Concentrations of platinum compounds or complexes in the liquid phase between $10^{-6}$ moles/liter and $10^{-1}$ moles/liter can be used. Higher molar concentrations (i.e. molarities) even to the extent of 1 mole/liter and higher may be used if desired.

The novel process is run most conveniently in the presence of an inert diluent. A variety of solvents can be used including ketones such as acetone, methyl ethyl ketone, methyl isobutyl ketone, acetophenone, and cyclohexanone, aromatics such as benzene, toluene and xylenes, halogenated aromatics including orthodichlorobenzene, ethers such as tetrahydrofuran, dimethoxyethane and dioxane, halogenated paraffins including methylene chloride, paraffins such as isooctane and other solvents such as acetonitrile.

The process of this invention will be further described by the following illustrative embodiments which are provided for illustration and are not to be construed as limiting the invention. Illustrative Embodiment I is described in detail, while the other examples employ the procedure of Illustrative Embodiment I with variation of catalysts, reactants and reaction conditions. Certain abbreviations are employed such as Ph for phenyl group, Bu for butyl group, Me for methyl group, n for normal.

Illustrative Embodiments

Metal complexes of the general formula cis-$PtCl_2(PR_3)_2$ were used for the preparation of the cationic species. The metal complex $PtCl_2(PPh_3)_2$ was used as purchased from Strem. The complexes $PtCl_2(P(p-PhCl)_3)_2$, $PtCl_2(P(m-PhCH_3)_3)_2$, $PtCl_2(P(p-PhOCH_3)_3)_2$ were prepared by the method detailed by Bailar and Itatani (Inorg. Chem., 11, 1618 (1965)) for cis-$PtCl_2(PPh_3)_2$. The complex cis-$PtCl_2(AsPh_3)_2$ was prepared as reported by Jensen (Zeit. Anorg. Chem., 229, 225 (1936)); cis-$PtCl_2(PnBu_3)_2$ was prepared as described by Kauffman et al. (Inorg. Syn., 7, 245 (1963)). The metal complexes $PtCl_2$ $(P(OPh)_3)_2$ and $PtCl_2(P(p-OPhCl)_3)_2$ were prepared by the addition of 2 equiv. of ligand to a solution of $PtCl_2(C_6H_5CN)_2$. All solvents and substrates were reagents grade and used without further purification.

Batch hydroformylation reactions were performed in a magnetically-driven 316SS 100 ml autoclave, equipped with a sampling tube.

Analyses were made by gas chromatography (GC), GC-MS, NMR and ESCA.

Preparation of [PtCl(CO) (PP$_3$)$_2$]ClO$_4$

A methylene chloride solution (20 ml.) of PtCl$_2$(PPh$_3$)$_2$(0.2 g, 0.25 mmol) in a Fisher-Porter bottle was saturated with CO by purging 3 times with 50 psig CO, then stirred with 50 psig (3.5 kg/cm$^2$) CO for 5 minutes. To this solution was added 0.06 g of AgClO$_4$ (0.29 mmol), which was then repressured to 50 psig with CO and stirred for ½ hour at room temperature. The resultant mixture was filtered to remove precipitated AgCl to yield a methylene chloride solution of [PtCl(CO) (PPh$_3$)$_2$]ClO$_4$ verified by infrared analysis which was used directly for the hydroformylation experiment.

Hydroformylation of Hexene-2

To a 100 ml-SS autoclave was added 5.0 ml of hexene-2 (40.3 mmol), 0.28 g of SnCl$_2$.2H$_2$0 (1.24 mmol), a CH$_2$Cl$_2$ solution of [PtCl(CO) (PR$_3$)$_2$]ClO$_4$ (0.25 mmol), and the total liquid volume brought up to 39 ml with the addition of more CH$_2$Cl$_2$. The autoclave was sealed, purged with nitrogen, and pressured to 500 psig (35 kg/cm$^2$) with CO/H$_2$ (1:1). The temperature was brought up to 120° C. rapidly. At the end of 3 hours, the reaction was cooled and the product solution analyzed chromatographically. The results were shown in Table I and illustrate the results using different stabilizing ligands.

Table I

Homogeneous Hydroformylation of Hexene-2. Ligand Dependence

Conditions: 100 ml-SS Autoclave, Hexene-2 (5 ml, 40.3 mmol), CH$_2$Cl$_2$ Solvent, Total Liquid Volume 39 ml, 120° C., 500 psig CO/H$_2$ (1:1) Initial Ratio, 3 hrs., Catalyst System: [PtCl (CO)(PR$_3$)$_2$]ClO$_4$/SnCl$_2$ . 2H$_2$O (0.25 mmol/1.24 mmol)

| Example | 1 | 2 | 3 | 4 | 5 |
|---|---|---|---|---|---|
| PR$_3$, stabilizing ligand | PnBu$_3$ | P(p-PhOMe)$_3$ | P(m-PhMe)$_3$ | PPh$_3$ | P(OPh)$_3$ |
| Conversion (%m) | 11.2 | 7.8 | 7.6 | 9.3 | 26.4 |
| Selectivity (%m) | | | | | |
| Aldehyde | 70.2 | 65.8 | 62.6 | 62.6 | 52.4 |
| Hexane | 20.4 | 30.3 | 29.8 | 26.5 | 40.2 |
| Linearity of | | | | | |
| Aldehyde (%) | 47.0 | 55.1 | 56.2 | 60.4 | 51.7 |
| Rate (m/m/hr) | 6 | 4 | 4 | 5 | 14 |

The above was repeated at a total pressure of 2000 psig (140 kg/cm$^2$). The results are shown in Table II.

Table II

Homogeneous Hydroformylation of Hexene-2. Ligand Dependence

Conditions: 100 ml-SS Autoclave, Hexene-2 (5 ml, 40.3 mmol), CH$_2$Cl$_2$ Solvent, Total Liquid Volume 39 ml, 120° C., 2000 psig CO/H$_2$ (1:1) Initial Ratio, 3 hrs., Catalyst System: [PtCl(CO) (PR$_3$)$_2$]ClO$_4$/SnCl$_2$ . 2H$_2$O (0.25 mmol/1.24 mmol)

| Example | 6 | 7 | 8 | 9 |
|---|---|---|---|---|
| PR$_3$ | P(n-Bu)$_3$ | P(m-PhMe)$_3$ | PPh$_3$ | P(OPh)$_3$ |
| Conversion (% m) | 39.1 | 31.7 | 35.2 | 65.2 |
| Selectivity (% m) | | | | |
| Aldehyde | 88.8 | 83.6 | 89.4 | 68.0 |
| Hexane | 8.3 | 14.0 | 10.0 | 27.2 |
| Linearity of | | | | |
| Aldehyde (%) | 25.9 | 34.0 | 34.3 | 35.6 |
| Rate (m/m/hr) | 21 | 18 | 19 | 35 |

The above was repeated with varying reaction temperatures. The results are shown in Table III.

Table III

Homogeneous Hydroformylation of Hexene-2. Temperature Dependence

Conditions: 100 ml-SS Autoclave, Hexene-2 (5 ml, 40.3 mmol), CH$_2$Cl$_2$ Solvent, Total Liquid Volume 39 ml, 2000 psig CO/H$_2$ (1:1) Initial Ratio, 3 hrs., Catalyst System: [PtCl(CO) (PPh$_3$)$_2$]ClO$_4$/SnCl$_2$ . 2H$_2$O (0.25 mmol/1.24 mmol)

| Example | 10 | 11 | 12 | 13 | 14 |
|---|---|---|---|---|---|
| Temperature, °C. | 80 | 100 | 120 | 140 | 180 |
| Conversion (%m) | 11.3 | 29.9 | 35.2 | 34.4 | 59.4 |
| Selectivity (%m) | | | | | |
| Aldehyde | 92.5 | 89.2 | 89.4 | 78.4 | 5.9 |
| Hexane | 4.8 | 7.3 | 10.0 | 20.4 | 16.8 |
| Linearity of | | | | | |
| Aldehyde (%) | 18.7 | 24.6 | 34.3 | 45.0 | 29.9 |
| Rate (m/m/hr) | 6 | 16 | 19 | 18 | 32 |

Repeating the above, but varying the pressure produces the following results of Table IV.

Table IV

Homogeneous Hydroformylation of Hexene-2. Pressure Dependence

Conditions: 100 ml-SS Autoclave, Hexene-2 (5 ml, 40.3 mmol), CH$_2$Cl$_2$ Solvent, Total Liquid Volume 39 ml, 120° C., CO/H$_2$ (1:1) Initial Ratio, 3 hrs., Catalyst System: [PtCl(CO) (PPh$_3$)$_2$]ClO$_4$/SnCl$_2$ . 2H$_2$O (0.25 mmol/1.24 mmol)

| Example | 15 | 16 | 17 | 18 |
|---|---|---|---|---|
| Pressure (psig) | 100 | 500 | 1000 | 2000 |
| Conversion (%m) | 1.5 | 9.3 | 18.0 | 35.2 |
| Selectivity (%m) | | | | |
| Aldehyde | 15.7 | 62.6 | 78.4 | 89.4 |
| Hexane | 50.2 | 26.5 | 18.2 | 10.0 |
| Linearity of | | | | |
| Aldehyde (%) | 75.6 | 60.4 | 49.9 | 34.3 |
| Rate (m/m/hr) | 1 | 5 | 10 | 19 |

Table V shows the results of varying the CO/H$_2$ ratio.

Table V

Homogeneous Hydroformylation of Hexene-2. SYN Gas Compositional Dependence

Conditions: 100 ml-SS Autoclave, Hexene-2 (5 ml, 40.3 mmol), CH$_2$Cl$_2$ Solvent, Total Liquid Volume 39 ml, 120° C. 500 psig CO/H$_2$ Initial, 3 hrs., Catalyst System: [PtCl(CO) (PPh$_3$)$_2$]ClO$_4$/SnCl$_2$ . 2H$_2$O (0.25 mmol/1.24 mmol)

| Example | 19 | 20 | 21 |
|---|---|---|---|
| CO/H$_2$ Ratio | 1:1 | 3:1 | 6:1 |
| Conversion (%m) | 9.3 | 5.9 | 2.9 |
| Selectivity (%m) | | | |
| Aldehyde | 62.6 | 73.4 | 72.0 |
| Hexane | 26.5 | 20.6 | 16.9 |
| Linearity of | | | |

Table V-continued

Homogeneous Hydroformylation of Hexene-2.
SYN Gas Compositional Dependence

Conditions: 100 ml-SS Autoclave, Hexene-2 (5 ml, 40.3 mmol),
CH$_2$Cl$_2$ Solvent, Total Liquid Volume 39 ml, 120° C.
500 psig CO/H$_2$ Initial, 3 hrs., Catalyst System:
[PtCl(CO) (PPh$_3$)$_2$]ClO$_4$/SnCl$_2$ . 2H$_2$O
(0.25 mmol/1.24 mmol)

| Example | 19 | 20 | 21 |
|---|---|---|---|
| Aldehyde (%) | 60.4 | 57.0 | 59.2 |
| Rate (m/m/hr) | 5 | 3 | 2 |

The above experimental procedures were repeated but using trans-5-decene as a feed in place of the 2-hexene. The results are given in Table VI.

Table VI

Homogeneous Hydroformylation of Trans-5-decene

Conditions: 100 ml-SS Autoclave, trans-5-Decene (5 ml, 26.4 mmol),
CH$_2$Cl$_2$ Solvent, Total Liquid Volume 39 ml, 100° C., 2000
psi CO/H$_2$ (1:1) Initial Ratio, 3 hrs., Catalyst System:
[PtCl(CO) (PR$_3$)$_2$]ClO$_4$/SnCl$_2$ . 2H$_2$O (0.25 mmol/1.24 mmol)

| | 22 | 23 | 24 | 25 | 26 | 27 |
|---|---|---|---|---|---|---|
| PR$_3$ | PnBu$_3$ | PPh$_3$ | P(PhCl)$_3$ | P(OPh)$_3$ | P(OPhCl)$_3$ | AsPh$_3$ |
| Conversion (%m) | 36.3 | 37.6 | 22.9 | 72.5 | 50.8 | 36.2 |
| Selectivity (%m) | | | | | | |
| Aldehyde | 91.9 | 95.0 | 98.4 | 84.1 | 87.1 | 78.9 |
| Decane | 2.8 | 5.0 | 1.6 | 15.9 | 12.9 | 21.0 |
| Linearity of | | | | | | |
| Aldehyde (%) | 15.6 | 14.6 | 10.4 | 17.3 | 17.2 | 9.7 |
| Rate (m/m/hr) | 13 | 13 | 8 | 26 | 18 | 17 |

The above experimental procedures were repeated but using a catalyst of the prior art (Knifton et al, U.S. 3,996,293 and U.S. 3,981,925). The results are given in Table VII. No linear aldehydes were detected.

Table VII

Homogeneous Hydroformylation of Trans-5-decene

Conditions: 100 ml-SS Autoclave, trans-5-decene (5 ml, 26.4
mmol), CH$_2$Cl$_2$ Solvent, Total Liquid Volume 39 ml,
80° C., 2000 psi CO/H$_2$ (1:1) Initial Ratio, 3 hrs.,
Catalyst System: PtCl$_2$(PPH$_3$)$_2$/SnCl$_2$ (0.25 mmol/
1.24 mmol)

| | 28 |
|---|---|
| Conversion (%m) | 8.2 |
| Selectivity (%m) | |
| Aldehyde | 95.5 |
| Linearity of | |
| Aldehyde (%) | 0 |

The above experimental procedures were repeated using a random C$_{13}$ internal olefin as feedstock. This olefin contained greater than 96%m C$_{13}$, balance consists of other carbon number olefins. This feed contained approximately 1.4%m of the 1-olefin isomer, 23.0%m of 2-olefin, 20.0% of 3-olefin, 55.6%m of 4,5,6-olefin and other impurities as determined by NMR.

Table VIII

Homogeneous Hydroformulation of C$_{13}$ Internal Olefin

Conditions: 100 ml-SS Autoclave, C$_{13}$ olefin (5.0 g, 27.4 mmol),
CH$_2$Cl$_2$ Solvent, Total Liquid Volume 39 ml, Catalyst
System: [PtCl(CO) (PPh$_3$)$_2$]ClO$_4$/SnCl$_2$ . 2L$_2$O (0.25 mmol/1.24 mmol)

| Example | Time (hr) | Temp (°C.) | Pressure [psig CO/4$_2$ (3:1)] | Conversion (%m) | Select to Aldehyde (%m) | Aldehyde Linearity (%) | Rate (m/m/hr) |
|---|---|---|---|---|---|---|---|
| 29 | 6 | 120 | 500 | 9.6 | 98.6 | 39.8 | |
| | 20 | 120 | 500 | 16.2 | 98.5 | 35.8 | 1 |
| 30 | 3 | 120 | 1000 | 7.0 | 96.0 | 35.3 | 3 |
| 31 | 3 | 140 | 1000 | 5.5 | 95.2 | 31.5 | |
| | 20 | 140 | 1000 | 21.4 | 98.9 | 24.0 | 1 |
| 32 | 3 | 120 | 1500 | 8.5 | 97.6 | 32.1 | 3 |
| 33[a] | 3 | 120 | 1500 | 9.8 | 95.2 | 28.7 | |
| | 20 | 120 | 1500 | 19.6 | 98.5 | 27.4 | 1 |

[a] Pre-equilibration with 1125 psi CO at 120° C. for 0.5 hr.

What is claimed is:

1. A process for preparing substantial amounts of linear aldehydes by hydroformylating internal olefins having 4 to about 30 carbon atoms, by contacting said olefins with carbon monoxide, and hydrogen at a temperature of from about 25° C. to about 180° C. and a pressure ranging from about 5 kg/cm$^2$ to about 200 kg/cm$^2$ in the presence of a catalyst comprising:

(a) a platinum complex having the following formula:

$$PtCl(CO)L_2^+ An^-$$

wherein An$^-$ is BPh$_4^-$, BF$_4^-$, ClO$_4^-$, PF$_6^-$, NO$_3^-$ or SiF$_6^{--}$ and L is a complexing ligand having the formula:

$$(RO)_a BR_b$$

wherein B is phosphorus, arsenic, antimony or bismuth, R is aryl, alkyl, aralkyl or alkaryl with less than 20 carbon atoms, wherein R is the same or different, a is an integer from 0 to 3, 0 has a value of 3-a; and (b) a modifying metal halide selected from SnCl$_2$, ZnCl$_2$, and GeCl$_2$ where the mole ratio of said metal halide to said platinum complex ranges from about 1 to about 100.

2. The process of claim 1 wherein the molar ratio of hydrogen to carbon monoxide ranges from about 10:1 to about 1:10.

3. The process of claim 1 wherein the temperature ranges from about 50° C. to about 140° C. and the pressure ranges from about 5 kg/cm$^2$ to about 140 kg/cm$^2$.

4. The process of claim 1 wherein excess complexing ligand L is present in the reaction mixture in amount of about 10 molar excess over stoichiometric requirements.

* * * * *